(12) United States Patent
Adachi et al.

(10) Patent No.: US 6,870,161 B2
(45) Date of Patent: Mar. 22, 2005

(54) APPARATUS FOR PROCESSING AND OBSERVING A SAMPLE

(75) Inventors: Tatsuya Adachi, Chiba (JP); Toshiaki Fujii, Chiba (JP); Hiroshi Sawaragi, Chiba (JP); Yasuhiko Sugiyama, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 10/644,696

(22) Filed: Aug. 20, 2003

(65) Prior Publication Data

US 2004/0129897 A1 Jul. 8, 2004

(30) Foreign Application Priority Data

Aug. 30, 2002 (JP) .................................... 2002-254881

(51) Int. Cl.[7] .............................. G01N 1/04; H01J 37/26
(52) U.S. Cl. .................... 250/311; 250/310; 250/492.2; 250/492.3; 250/491.1
(58) Field of Search .............................. 250/310, 311, 250/307, 492.2, 492.3, 491.1

(56) References Cited

U.S. PATENT DOCUMENTS

2002/0050565 A1 * 5/2002 Tokuda et al. .............. 250/310

* cited by examiner

Primary Examiner—Nikita Wells
(74) Attorney, Agent, or Firm—Adams & Wilks

(57) ABSTRACT

An apparatus for processing and observing a sample has a sample stage for supporting a sample at a preselected location thereof, a focused ion beam irradiation system for irradiating the sample with a focused ion beam along an optical axis to cut out a portion from the sample, and a side entry stage disposed over the sample stage and extending slantingly with respect to the optical axis of the focused ion beam irradiated by the focused ion beam irradiation system. The side entry stage has a microscope sample holder for picking up the cut-out sample portion directly from the preselected location of the sample and for supporting the sample portion. The microscope sample holder is configured to be removed from the side entry stage while supporting the sample portion and to be connected to an entry stage of a microscope device for observing the sample portion.

20 Claims, 14 Drawing Sheets

APPARATUS FOR PROCESSING AND OBSERVING A SAMPLE

BACKGROUND OF THE INVENTION

1. Technical Field

The present invention relates to a sample manufacturing apparatus and, more specifically, to an apparatus for making test pieces for slice observation from a wafer with a transmission electron microscope (hereafter referred to as TEM) or a scanning electron microscope (hereafter referred to as SEM) utilizing ultra-fine processing using a focused ion beam (hereafter referred to as FIB).

2. Related Art

An FIB device is known as a device for manufacturing a test piece such a TEM sample or an SEM sample from a wafer, being an original sample. A schematic drawing of an FIB device of the related art is shown in FIG. 10. The main components of this FIB device are an ion source 100, an ion optical system 101, a secondary charged particle detector 102, a gas gun 103, a sample holder 104 and a sample stage 105.

The ion source 100 is a liquid metal ion source exemplified by, for example, gallium (Ga). The ion optical system 101 is for focusing an ion beam from the ion source 100 and is comprised of a condenser lens (electrostatic lens) a beam blanker, a movable aperture, an 8-pole stigmeter, an objective lens (electrostatic lens) and a scanning electrode. The secondary charged particle detector 102 detects secondary charged particles generated when an ion beam 100a is scanned on the sample 106, and a scanning ion microscope (hereafter referred to simply as SIM) function is provided by carrying out image processing based on the detection results. The sample stage 105 is a stage capable of movement on 5 axes of control. With 5 axes of control it is possible to achieve 3-dimensional movement in the XYZ directions, rotation around an axis orthogonal to the XY plane, and tilt control. The sample holder 104 is for fixing the sample 106, and is mounted on a movable platform called a base (not shown in the drawings) and conveyed on to the sample stage 105. The gas gun 103 sprays gas for forming a deposition film as a protective film onto the surface of the sample 106.

There are basically the following two methods in sample manufacture using the above described FIB device. One is a method of fixing a small sample that has been subjected to preliminary processing by cutting away part of a wafer using a dicing saw on a holding member, fixing this to a sample holder 104 as a sample 106, and processing using an ion beam 100a. Another is a so-called pick-up method (or lift-out method) where the wafer itself is fixed to the sample holder 104 as the sample 106, a specific site on the sample holder 104 is directly processed by the ion beam 100a, and the test piece taken out. The latter method can manufacture a test piece (TEM sample or SEM sample) without dividing the original sample, which means that compared to the former method which splits the wafer to make a small piece, there are the merits that it is advantageous with respect to cost, and the sample manufacturing time is short.

FIG. 11 schematically shows a sequence of manufacturing processes for a TEM sample using the pick-up method, in which the FIB device shown in FIG. 10 is used. The manufacturing processes for a TEM sample will be described in the following with reference to FIG. 10 and FIG. 11.

First, a wafer, being the sample 106, is fixed onto the sample stage 105, and based on previously provided position information for a specific site rough alignment is carried out so that the ion beam 100a is irradiated close to that specific site. Next, the vicinity of a fault site is scanned with the ion beam 100a, and the position of a fault site is specified while looking at an SIM image obtained by this scanning (position output). After position output, deposition gas is sprayed onto the surface of the wafer using the gas gun 103, and a deposition film (protective film) for the surface of the wafer is formed by scanning a specified range containing the specific site with the ion beam 100a. Formation of this deposition film is generally called ion assist deposition (or ion beam CVD (Chemical Vapor Deposition), and it is possible to selectively form a deposition film on sections irradiated by the ion beam 100a.

Next, as shown in FIG. 11A, the ion beam 100a is irradiated to the vicinity of the specific site of the wafer surface to perform general processing, and the ion beam 100a is also irradiated to that processed section to perform finishing processing. With this processing, the ion beam 100a is irradiated from a normal direction with respect to the surface of the wafer, which means that the region irradiated by the ion beam 100a is gradually removed from the wafer surface, to obtain the slice 107a as shown in FIG. 11B. The extent to which the thickness of the slice 107a section looking from above is made thinner is different depending on the material of the sample and the acceleration voltage of a TEM used. For example, in the case of lattice image observation of an Si type semiconductor sample with a 200 kV acceleration voltage TEM, this must be 0.1 µm or less. Also, in the case of carrying out 3D analysis with tomography using a TEM, the sample thickness is finished to about 0.5 µm.

After formation of the slice 107a, the angle of incidence of the ion beam 100a to the wafer is adjusted by controlling the tilt angle of the sample stage 105, and a notch 107b as shown in FIG. 11B (the section shown by a dotted line in FIG. 11B) is formed around the section where the slice 107a is formed by processing using the ion beam 100a. A part at an upper surface side remains that is not notched, and a section taken out along the notch 107b is the TEM sample 107.

A manipulator, not shown, is used in taking out the TEM sample 107. A tip of a probe 108, made of a glass material, is brought close to a lateral slice 107a of the TEM sample 107. If the tip of the probe 108 is brought sufficiently close to the slice 107a, then as shown in FIG. 11C, the TEM sample 107 is attracted to the probe 108 due to static electricity. Then, with the TEM sample 107 still stuck to the tip, the probe 108 is mode onto a fixing table (not shown) that has been separately prepared, and the TEM sample 107 stuck to the tip is fixed to a specified part of the fixing table. In fixing the TEM sample 107 to the fixing table at this time, it is possible to utilize deposition processing or static electricity. Depending on the situation, it may also be possible to perform finishing processing for the TEM sample 107 fixed to the fixing table using the ion beam 100a.

When carrying out TEM observation, the fixing table to which the above described TEM sample 107 is fixed is taken out from the FIB device, and attached to a separately prepared TEM sample holder. This TEM sample holder is then fitted into an entry stage of a TEM device that is separate from the FIB device, and the slice 107a of the TEM sample 107 is observed.

With manufacture of the TEM sample using the FIB device described above, outside the FIB device a fixing table to which the TEM sample 107 is fixed is attached to the TEM sample holder, and after TEM observation in the event that the TEM sample is processed again, it is necessary to remove the fixing table to which the TEM sample is fixed is from the TEM sample holder, fix the sample holder again, and convey onto the sample stage inside the FIB device. This is extremely bad from an operating point of view.

Recently, methods have been proposed where manufacture of a test piece, such as a TEM sample, and fixing to a sample holder for observation of the manufactured test piece (such as a TEM sample holder) can be carried out sequentially inside the FIB device. As one example, there is a sample manufacturing device as disclosed in Japanese Patent laid-open No. 2000-155081. FIG. 12 shows the schematic structure of this sample manufacturing device.

The sample manufacturing device shown in FIG. 12 has an FIB irradiation optical system 202, a secondary electron detector 203, a deposition gas source 204, a sample movement mechanism 206, a test piece probe movement mechanism 209 and an observation sample holder movement mechanism 211 provided in a sample processing chamber 201 that has been evacuated using a vacuum pump 200.

The sample movement mechanism 206 has an original sample 5 mounted thereon, and imparts relative displacement for an FIB original sample 5 irradiated from the FIB irradiation optical system 202 with respect to the original sample 5. The test piece probe movement mechanism 209 has a test piece probe holder 208 attached thereto, and enables three dimensional movement of the test piece probe holder 208. An observation sample holder 210 is attached to the observation sample holder movement mechanism 211, and three dimensional movement of the attached observation sample holder 210 is enabled. These movement mechanisms enable delivery of a test piece probe 207 between the test piece probe holder 208 and the observation sample holder 210.

With the above described sample manufacturing device, a specific site of a wafer, being the original sample 5, is processed by an FIB from the FIB irradiation optical system 202 to form a cantilever shaped test piece, a specific site of the test piece probe 207 held on the test piece probe holder 208 is brought into contact with part of this cantilever shaped test piece, and fixed by deposition processing. Also, part of the cantilever shape is processed by the FIB from the FIB irradiation optical system 202 to be cut away, and a test piece is separated from the original sample 5. The test piece probe 207 to which the separated test piece is fixed is then delivered from the test piece probe holder 208 to the observation sample holder 210.

As well as the above, there is an FIB sample manufacturing device provided with a side entry stage to which it is possible to attach a TEM sample holder, as disclosed in Japanese Patent Laid-open No. 2002-62226. FIG. 13 shows the schematic structure of this FIB manufacturing device.

The FIB manufacturing device shown in FIG. 13 has an ion beam irradiation system 301, a manipulator 305, a TEM sample stage 306, being a side entry stage, and a wafer sample stage 304, to which a wafer 303 is fixed, provided in an FIB sample chamber 302 that has been evacuated by an evacuation pump, not shown.

The vicinity of the center of the FIB sample chamber 302 constitutes an FIB processing position, and the ion beam irradiation system 301 is arranged so that the optical axis passes through the vicinity of the center of the FIB sample chamber 302. The TEM sample stage 306 is capable of movement in the horizontal direction (the direction of the arrow B), and it is possible to insert a TEM sample holder that is shared between this FIB sample manufacturing device and a separately prepared TEM device. The wafer sample stage 304 is provided with a movement mechanism for moving up an down in the vertical direction, that is, the direction of arrow A (Z direction) along the optical axis of the ion beam irradiation system 301 (central axis of the lens barrel).

With the above described FIB sample manufacturing device, first of all, after the TEM sample stage 306 has been made to retreat to a position that is sufficiently apart from the FIB processing position, the wafer sample stage 304 with the wafer 303 mounted thereon is moved to the FIB processing position. Then, a specific site of the wafer 303 is processed by an ion beam from the ion beam irradiation system 301, and part of that processed section is taken out and held by the manipulator 305 as a TEM test piece.

Next, as shown in FIG. 14, after the wafer sample stage 304 has been made to retreat to a position that is sufficiently apart from the FIB processing position, the TEM sample stage 306 to which a TEM sample holder 311 is attached is moved to the FIB processing position, and the previously held TEM test piece is fixed to a specified part of the TEM sample holder 311 using the manipulator 305. Then, an ion beam from the ion beam irradiation system 301 is irradiated to the test piece fixed to the TEM sample holder 311 to perform finishing processing.

According to the above described FIB sample manufacturing device, it is possible to carry out processing to manufacture a TEM test piece from a wafer and processing to fix the manufactured test piece to a TEM sample holder inside the FIB sample chamber. Further, when processing the TEM test piece again after TEM observation, it is possible to simply attach the TEM sample holder to the TEM sample stage of the FIB sample manufacturing device again.

As described above, with sample manufacture using the FIB device shown in FIG. 10, there is a problem that operability is bad.

In the sample manufacturing device disclosed in Japanese Patent Laid-open No. 2000-155081, since manufacture of a test piece and fixing of the manufactured test piece to a test piece observation sample holder within the FIB device is carried out sequentially, it is possible to solve the above described problem with respect to operability, However, in this case there is the following problem.

At the FIB device, since with the above described stricture it is not possible to make the sample processing chamber 203 very large, the FIB irradiation optical system 202, gas source 204, detector 203, sample movement mechanism 206, observation sample holder 210 and the test piece probe holder 208 are arranged close together in the limited space of the sample chamber 263. With the structure shown in FIG. 12, the observation sample holder 210 and the test piece probe holder 208 both have tips arranged in the horizontal direction so as to cross at the FIB processing position, and with this type of arrangement there is sometimes interference between each of the holders and the sample movement mechanism 206 arranged below the FIB processing position.

By causing the sample movement mechanism 206 to retreat sufficiently from the FIB processing position, it is possible to avoid interference with the holders, but in limited space it is difficult to ensure a space for retreating, and it is not practical. Also, if, for argument's sake, it was possible to ensure such a space, the sample processing chamber 203 would be enlarged by the extent of that space, and the device would be made larger. If the sample processing chamber 203 is made larger, it will become impossible to sufficiently evacuate the inside of the chamber. Also, because the stroke of the sample movement mechanism 206 will be made longer, there is a danger of FIB processing precision being lowered due to vibration.

In the FIB sample manufacturing device disclosed in Japanese patent laid-open No. 2002-62226 it is also possible to solve the above described issue regarding operability, but there is the following type of problem.

As shown in FIG. 13, the wafer sample stage 104 and the TEM sample stage 106 move respectively in the vertical direction and the horizontal direction so as not to interfere with each other. It is difficult to ensure this type of movement space in the limited space of the sample chamber, and is not really possible. Also, the device (sample chamber) is enlarged by the extent of any movement space provided, making the device bulky. Further, if the sample chamber is made larger, it will become impossible to sufficiently evacuate the inside of the sample chamber.

Also, in order to move the wafer sample holder 104 to a position where it does not interfere with the TEM sample stage 106, a certain stroke length is required. If the stroke length of the wafer sample stage 104 is made long, the FIB processing precision will be lowered due to vibration of the wafer sample stage 104.

The object of the present invention is to solve each of the above described problems in the conventional art, and to provide a compact sample manufacturing device in which a sample stage and an observation sample holder (side entry stage) do not interfere.

SUMMARY OF THE INVENTION

In order to achieve the above described object, a sample manufacturing device of the present invention comprises a sample stage to which an original sample is fixed, a focused ion beam irradiation system for irradiating a focused ion beam from a vertical direction to a specified place on the original sample fixed to the sample stage, and a side entry stage, arranged diagonally above the sample stage, for inserting a sample holder for specified observation in a diagonal direction with respect to the vertical direction, and supporting the inserted sample stage for observation so as to be capable of movement in the diagonal direction, wherein a test piece taken out from a specified place of the original sample is fixed to a tip section of the sample holder for specified observation supported on the side entry stage. With this structure, the sample holder for observation is configured so as to be inserted diagonally from above the sample stage, which means that compared to the related art where the sample holder is inserted in a horizontal direction, it is difficult for interference to arise between the sample holder for observation and the sample stage.

In the case described above, the side entry stage preferably has the sample holder for specified observation held so that a tip of the sample holder for specified observation is positioned in a space formed by removing the original sample from on the sample stage, and is further provided with a manipulator attached to a tip of the sample holder for specified observation held on the side entry stage for removing the test piece from a specified place on the original sample. With this structure, using a space made by removing the sample holder for specified observation to which the original sample is fixed from on the sample stage, the test piece is fixed to the sample holder for specified observation, which means that the sample stage can be made to retreat from the FIB processing position in order to prevent interference. In this way, according to this structure, the movement space for the sample stage (retreat space) that was required in the related art is no longer required, which means the device can be made more compact to the extent of that space.

Further, the sample holder for specified observation is provided with a needle on a tip, and the side entry stage is preferably configured so that the sample holder for specified observation is moved three dimensionally to cause the tip of the needle to come into contact with or approach a specified location of the original sample. In this configuration also, since the movement space for the sample stage for preventing interference that is required in the related art is no longer required, it is possible to make the device more compact to the extent of that space. In addition, since the manipulator is not required, it is possible to make the device compact and also to reduce cost by that extent.

In the invention described above, the focused ion beam irradiation system preferably has a structure comprising a lens barrel provided with first and second irradiation systems, the lens barrel being attached to a sample chamber housing the sample stage, and is further provided with a lens barrel internal entry stage, attached to the lens barrel at an outer side of the sample chamber, into which the sample holder for specified observation is inserted, the first irradiation system irradiating an ion beam to a specified place on the original sample fixed to the sample stage, and the second irradiation system irradiating an ion beam to the test piece fixed to a tip of the sample holder for specified observation inserted from the lens barrel internal entry stage. In this case, by using the lens barrel internal entry stage, processing precision of the test piece is improved.

DETAILED DESCRIPTION OF THE PREFERRED EMBODIMENTS

Next, embodiments of the present invention will be described with reference to the drawings.

(Embodiment 1)

Figure 1:
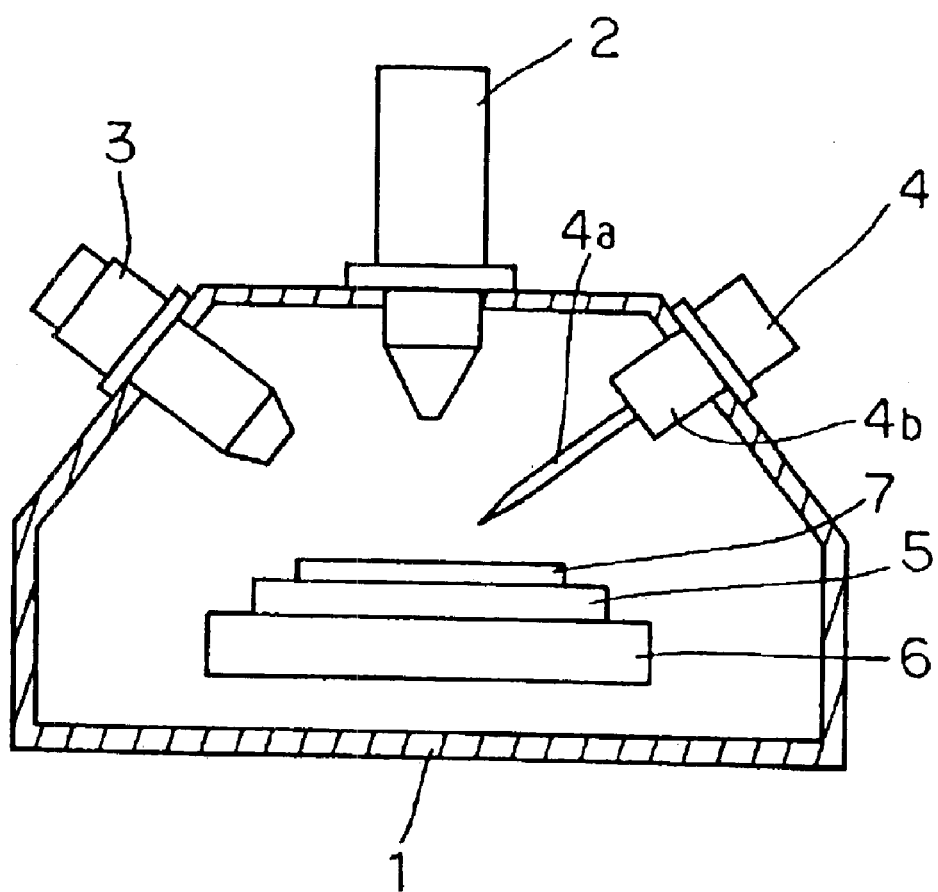
FIG. 1 is a schematic cross sectional drawing showing the structure of an FIB device of a first embodiment of a sample manufacturing device of the present invention.

FIG. 1 is a schematic cross sectional view showing the schematic structure of an FIB device of a first embodiment of a sample manufacturing device of the present invention. This FIB device is for manufacturing a test piece such as a TEM sample or an SEM sample from a wafer, being an original sample, using a pick-up method, and is provided with a sample chamber 1 that is evacuated using an evacuation pump, not shown, with an FIB irradiation optical system 2, a side entry stage 3, a manipulator 4 and a sample stage 6 being provided in this sample chamber 1. Besides this, although not shown in FIG. 1, structures required for FIB processing, such as a gas gun and a secondary charged particle detector, are also provided in the sample chamber 1.

Figure 10:
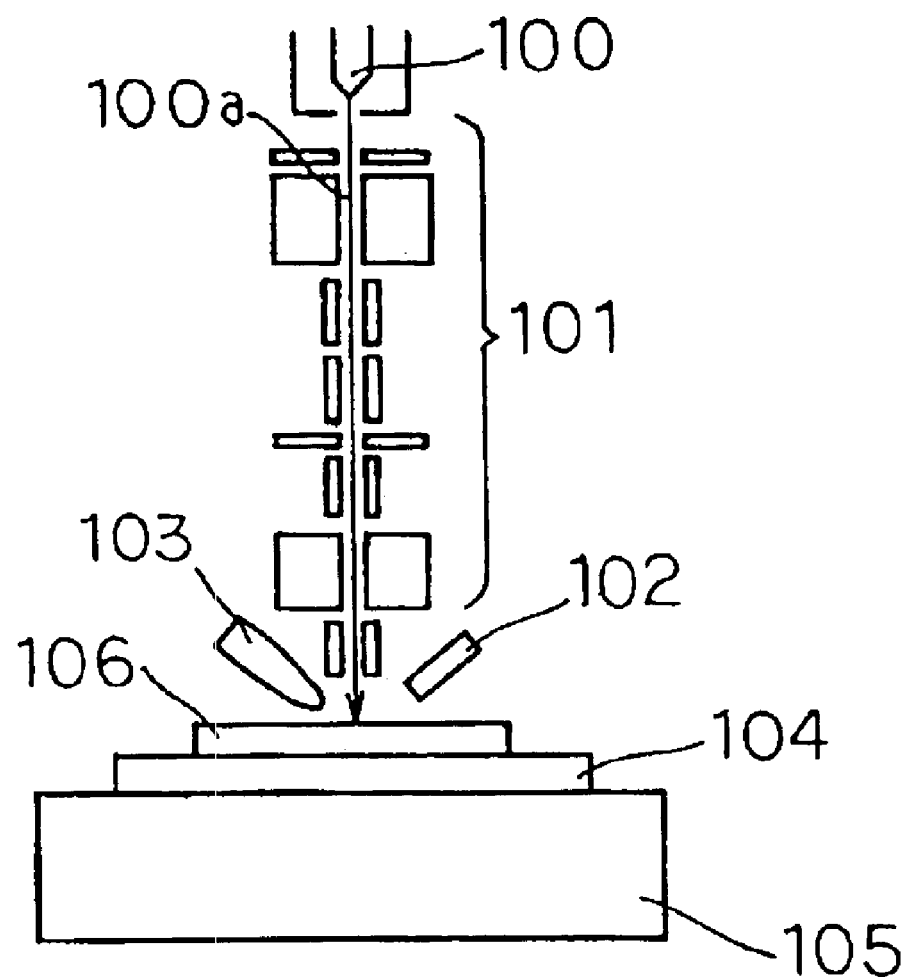
FIG. 10 is a schematic drawing schematically showing the outline structure of an FIB device of the related art.

A sample holder 5 for fixing an original sample 7, being a wafer, and the sample stage 6 are the same as shown in FIG. 10. The FIB irradiation optical system 2 is positioned above the sample stage 6, and can scan a specified location of the original sample 7 with a sufficiently focused ion beam. As the FIB irradiation optical system 2, there is provided a liquid metal ion source exemplified by, for example, gallium (Ga). Processing and deposition are carried out using an ion beam from the FIB irradiation optical system 2.

The manipulator 4 is made up of a probe 4a, and a movement mechanism 4b for moving the probe 4a three dimensionally. A micromotion mechanism capable of removing and fixing the test piece using a pick-up method is also included in the movement mechanism 4b. The side entry stage 3 can insert an observation sample holder (not shown) used in a TEM device or an SEM device from a diagonal direction with respect to the optical axis of the FIB irradiation optical system 2 (vertical direction), as well as move the inserted observation sample stage three dimensionally. The side entry stage 3 also has a spare chamber in which a well known airlock mechanism is provided, and it is possible to perform carrying in and carrying out of the observation sample stage from this spare chamber with the inside of the sample chamber 1 maintained in a vacuum state.

Figure 2:
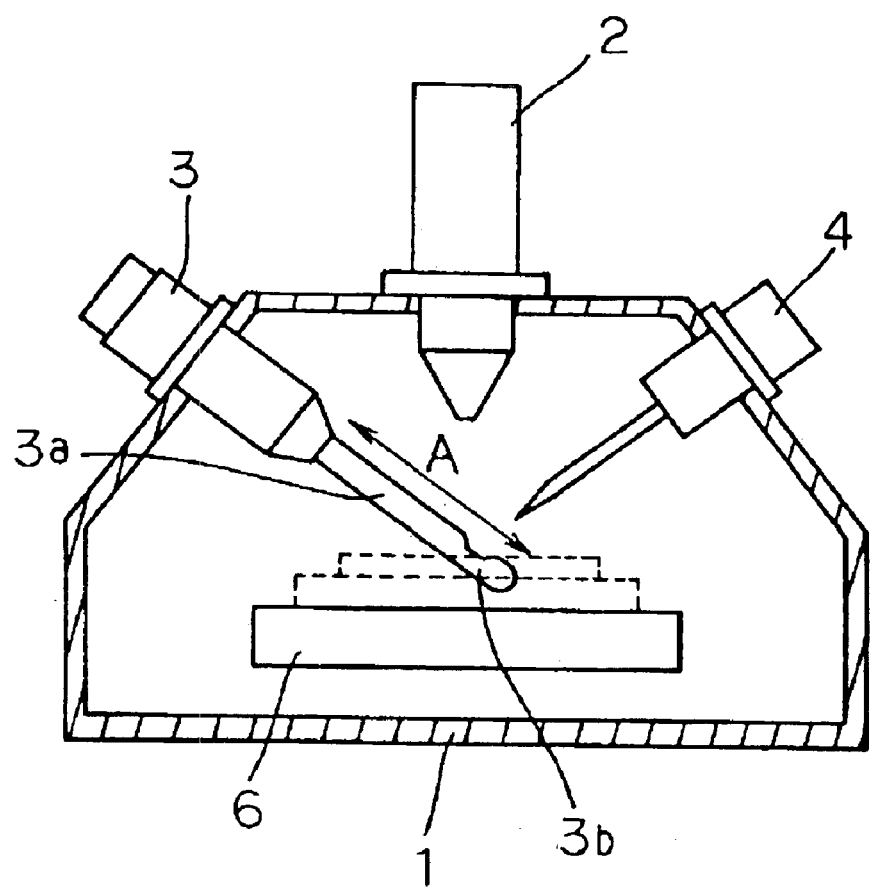
FIG. 2 is schematic drawing showing the state of a TEM sample holder attached to a side entry stage.

A state where a TEM sample holder is attached to the side entry stage 3 as an observation sample stage is shown in FIG. 2. In FIG. 2, a TEM sample holder 3a is a rod-shaped holder shared between this FIB device and a TEM device, and a TEM sample is fixed to a tip section 3b. The side entry stage 3 can move (stroke) in an insertion direction of the TEM sample holder 3a (arrow A in FIG. 2), and at the time of maximum stroke the tip section 3b is at the FIB processing position.

Figure 3A:
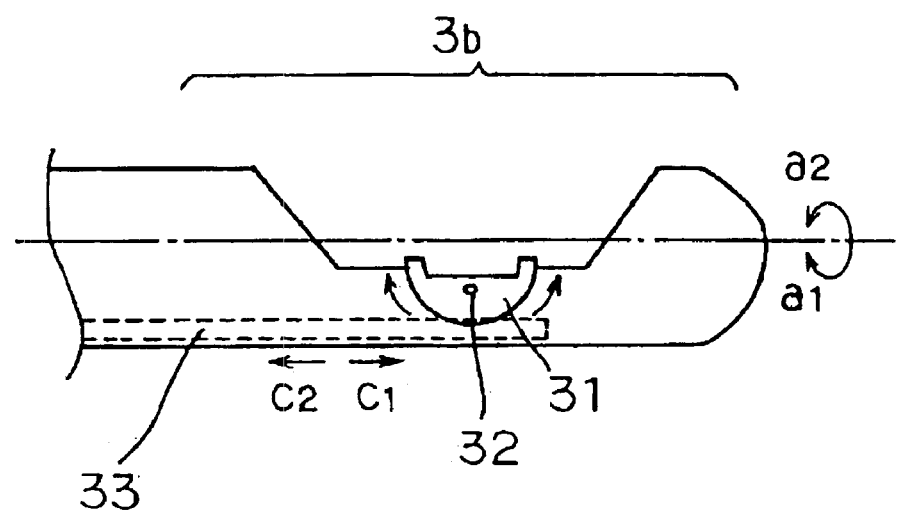
FIG. 3A is a cross sectional drawing schematically showing one example of the structure of a tip section of a TEM sample holder.
Figure 3B:
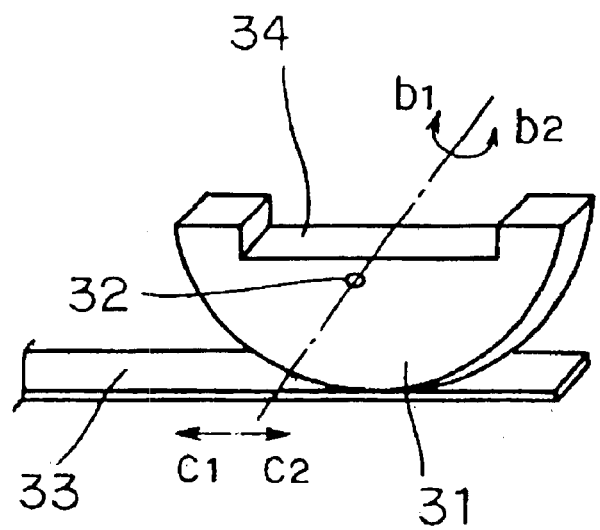
FIG. 3B is a perspective drawing schematically showing the structure of a holding section for holding a TEM sample, provided on the tip section shown in FIG. 3A.

The structure of the tip section 3b of the TEM sample holder 3a is shown in FIG. 3A, and the structure of a holding section for holding the TEM sample, provided on the tip section 3b, is shown in FIG. 3B. The TEM sample holder 3a is supported by the side entry stage 3 so as to be capable of movement in the directions of arrows a1 and a2 in FIG. 3. The tip section 3b is cut away into a U-shape looking from a direction orthogonal to the longitudinal direction of the TEM sample holder 3a, and a holding section 31 for fixing the TEM sample is provided in this cut-away section in a detachable manner.

The holding section 31 is semicircular in shape rotating centrally around a rotational axis 32, is provided with a mounting indent 34 for fixing the TEM sample, and is provided so that a circular arc section contacts a slide plate 33. The slide plate 33 is provided capable of sliding in the direction of arrows c1 and c2 in FIG. 3, along the longitudinal direction of the TEM sample holder 3a, and it is possible for the holding section 31 to rotate in the direction of arrows b1 and b2 in FIG. 3 by causing the slide plate 33 to slide in the direction of arrows c1 and c2.

Next, a manufacturing sequence for a test piece using the FIB device of this embodiment will be specifically described.

Figure 4A:
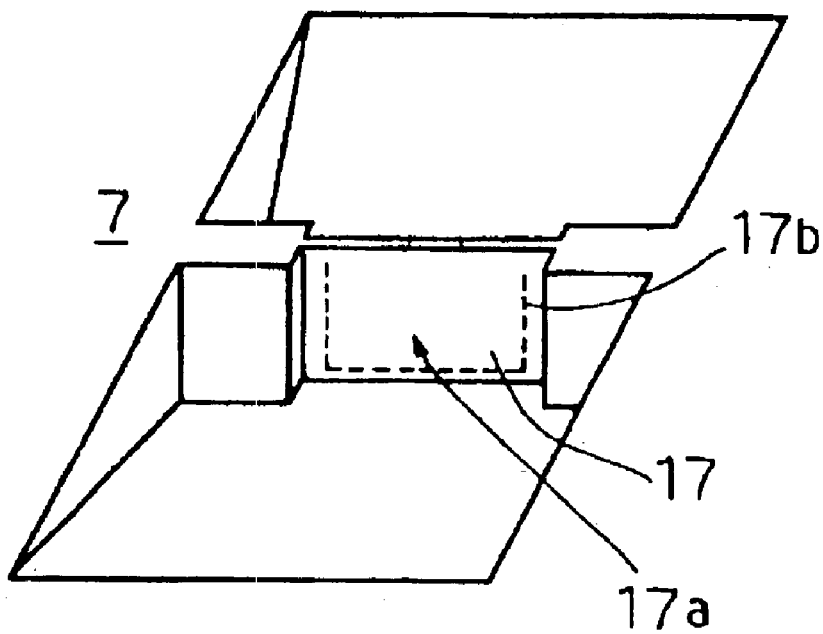
FIG. 4A and FIG. 4B are schematic drawings for describing a TEM manufacturing procedure carried out in the FIB device shown in FIG. 1.
Figure 4B:
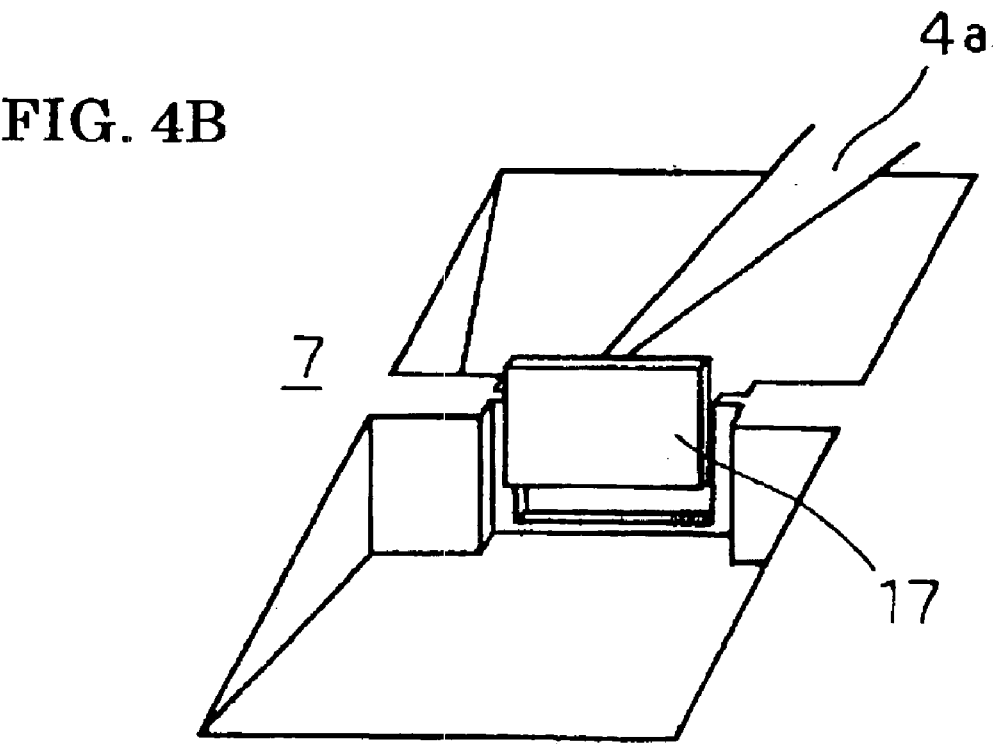
Figure 11A:
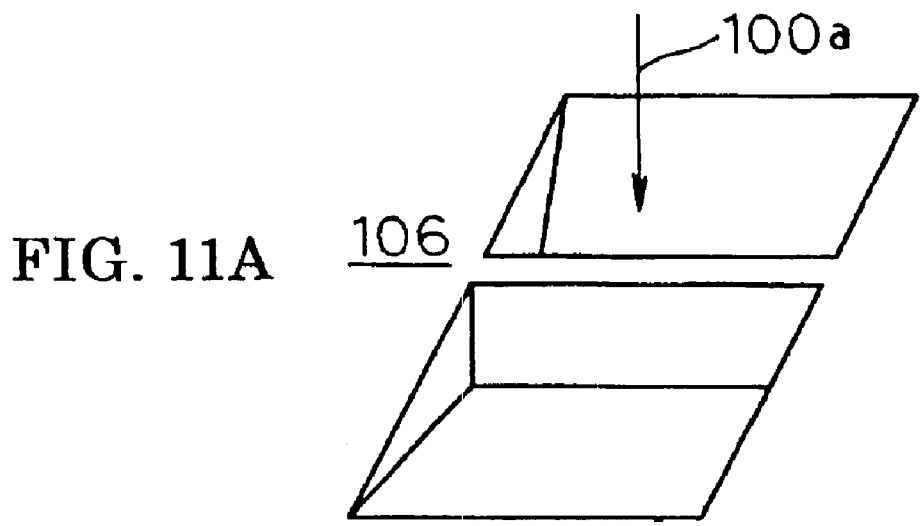
FIG. 11A–FIG. 11C are schematic drawings showing a series of manufacturing procedures for a TEM sample using a pick-up method, using the FIB device shown in FIG. 10.
Figure 11B:
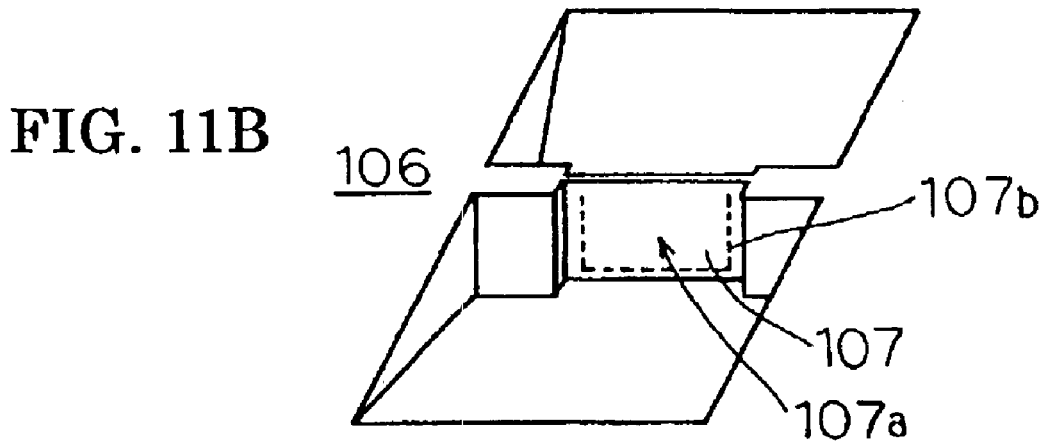
Figure 11C:
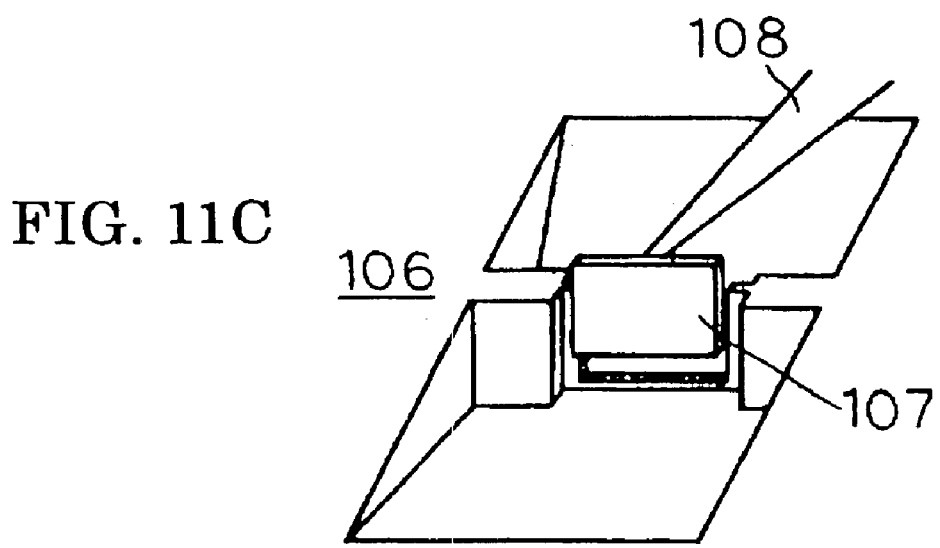
Figure 12:
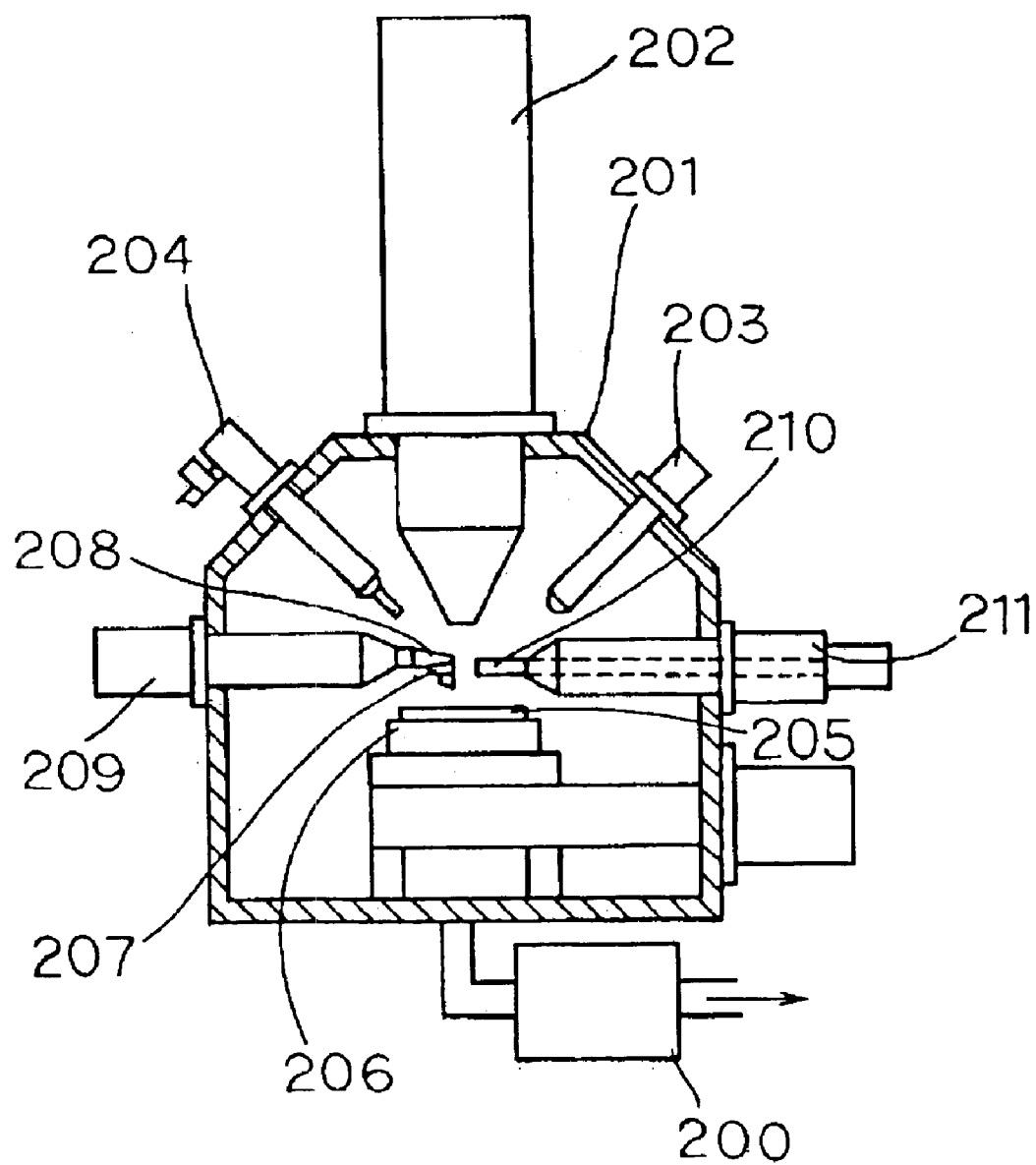
FIG. 12 is a cross sectional drawing showing the outline structure of a sample manufacturing device disclosed in Japanese Patent Laid-open No. 2000-155081.
Figure 13:
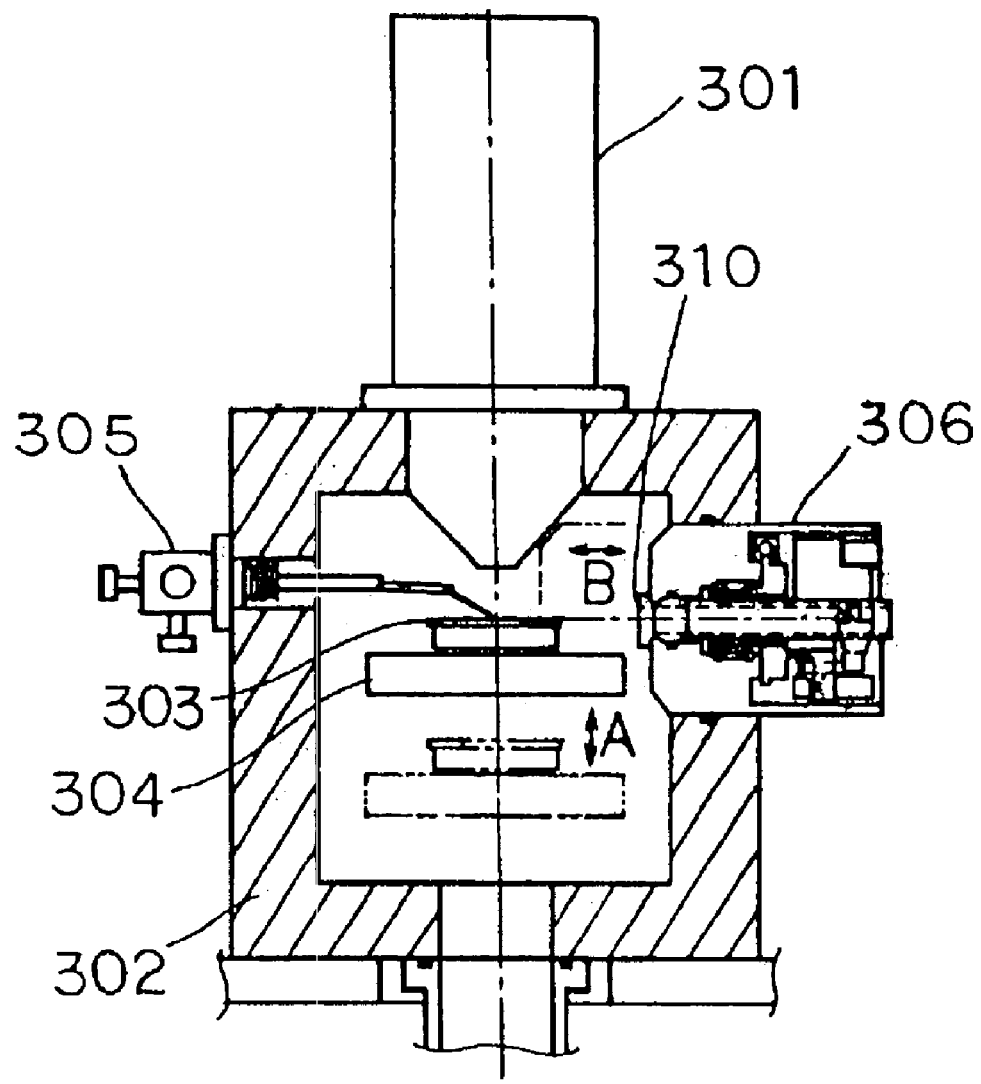
FIG. 13 is a cross sectional drawing showing the outline structure of a sample manufacturing device disclosed in Japanese Patent Laid-open No. 2002-62226.
Figure 14:
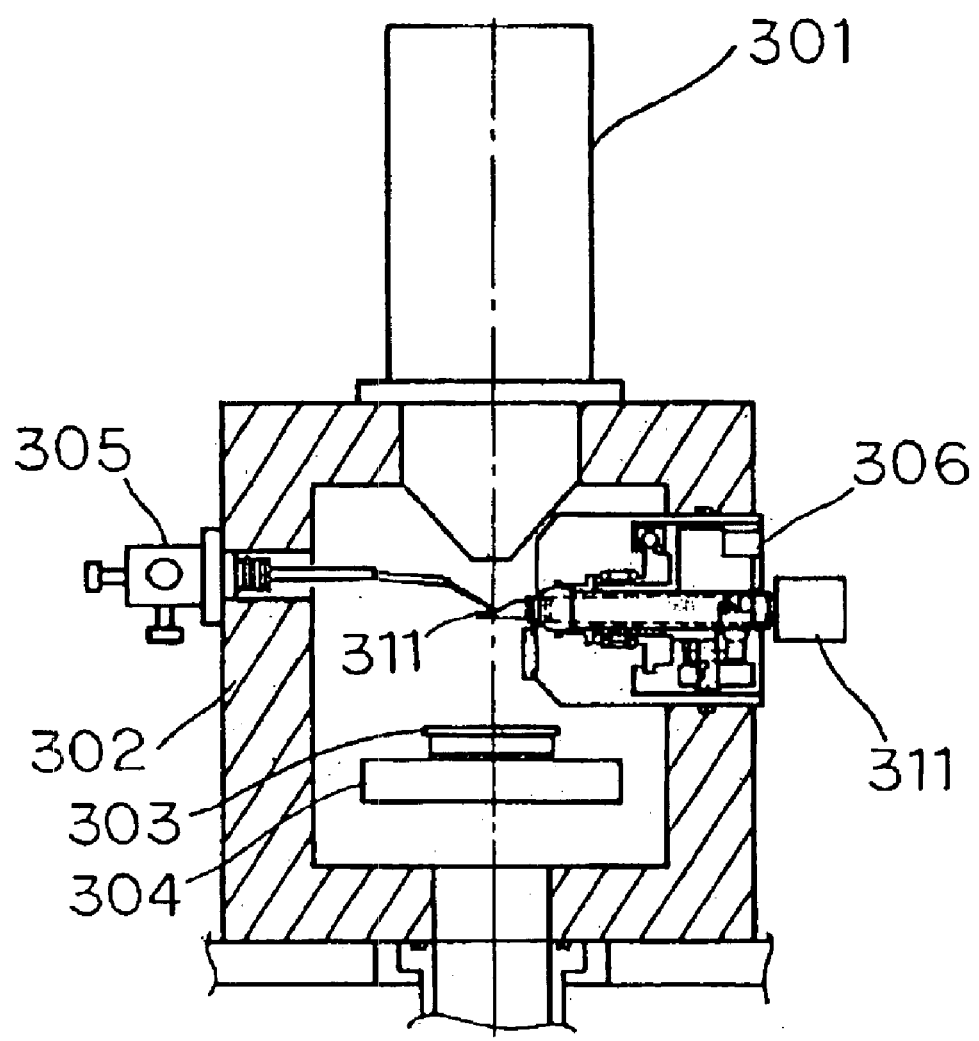
FIG. 14 is a schematic drawing for describing a TEM sample fixing operation for the FIB sample manufacturing device shown in FIG. 13.

First of all, according to the sequence shown in FIG. 11A and FIG. 11B described previously, a specified location of a wafer, being the original sample 7, is irradiated from a vertical direction with an ion beam from the FIB irradiation optical system 2 and processed, to form a TEM sample 17 having a slice 17a and notch 17b as shown in FIG. 4A. Then, as shown in FIG. 4B, the tip of the probe 4a is brought into contact with or close to the slice 17a of the TEM sample 17 using the manipulator 4, and the TEM sample 17 is separated from the original sample 7 by fixing the TEM sample 17 to the tip of the probe 4a by static electricity.

Figure 5A:
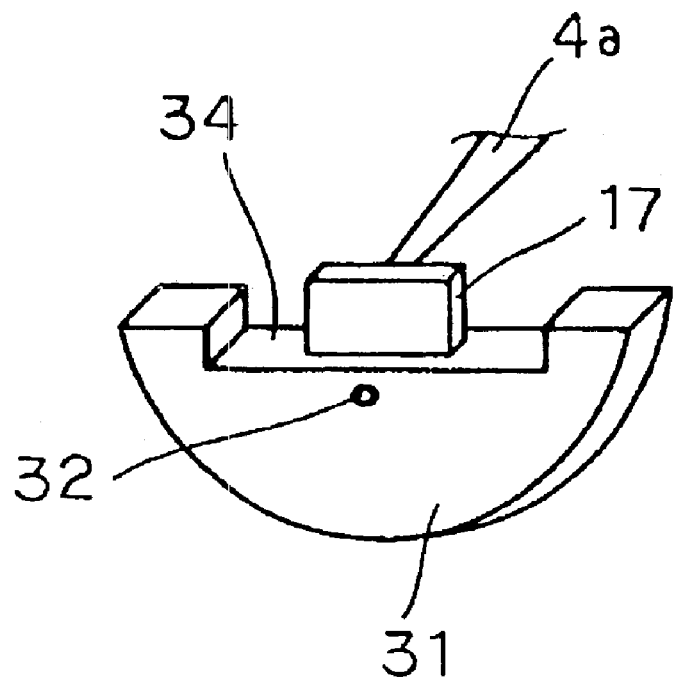
FIG. 5A and FIG. 5B are schematic drawings for describing a TEM sample fixing procedure carried out in the FIB device shown in FIG. 1.

Then, after causing the probe 4a having the TEM sample 17 fixed to the tip to retreat from the FIB processing position to remove the sample holder 5 to which the original sample 7 is fixed from on the sample stage 6, the TEM sample holder 3a is attached to the side entry stage 3, as shown in FIG. 2. The side entry stage 3 is made to slide so that the tip section 3b of the TEM sample holder 3a comes to the FIB processing position, and, using the manipulator 3 the bottom of the TEM sample 17 fixed to the tip of the probe 4a is brought into contact with the mounting indent 34 of the holding section 31, as shown in FIG. 5A. At the time of this contact, adjustment is carried out in advance using the slide plate 33 so that the surface of the mounting indent 34 of the holding section 31 becomes parallel to the horizontal direction.

Figure 5B:
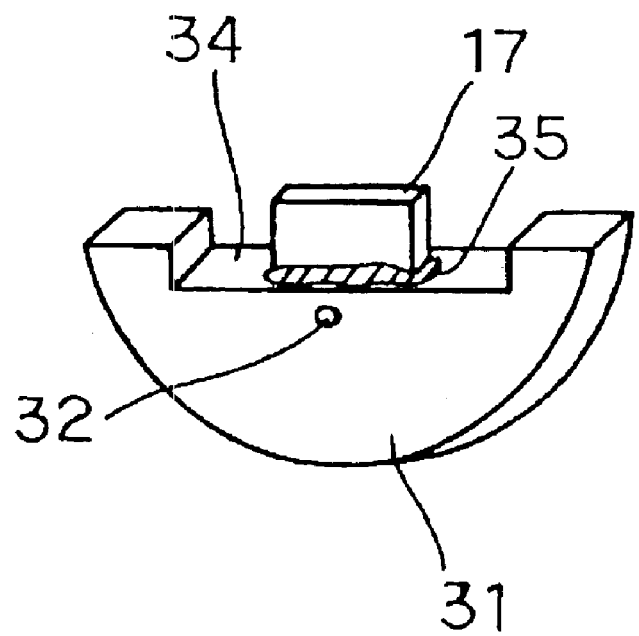

In the above described contact state, gas for deposition is jetted to contacting sections of the bottom of the TEM sample 17 and the mounting indent 34, and by then irradiating this section with an FIB from the FIB irradiation optical system 2 a deposition film 35 is selectively formed, as shown in FIG. 5B. The TEM sample 17 is fixed to the mounting indent 34 by this deposition film 35, and it is possible to separate the TEM sample 17 from the probe 4a. It is also possible to utilize static electricity in fixing the TEM sample 17 to the mounting indent 34.

Finally, final finishing processing is carried out using an FIB from the FIB irradiation optical system 2 for both slices 17a of the TEM sample 17 removed from the probe 4a and fixed to the mounting indent 34, to obtain a slice for observation.

When performing TEM observation, the TEM sample holder 3a is removed from the side entry stage 3, and attached to the entry stage of the TEM device. Then, inside the TEM device, the slice for observation of the TEM sample 17 is scanned with an electron beam to obtain a TEM image.

After TEM observation, if the TEM sample 17 is to be processed again the TEM sample holder 3a is preferably attached once more to the side entry stage 3.

According to the sample manufacturing device of the embodiment described above, since the side entry stage 3 is configured so that the TEM sample holder 3a, being the sample observation holder, is inserted not in the horizontal direction but in a direction diagonally up from the sample stage 6, a structure is realized with which it is difficult for the TEM sample holder 3a to interfere with the sample stage 6 compared to the related art type where the sample observation stage is inserted in the horizontal direction. Also, by causing the sample stage 6 to tilt in an opposite direction to the position where the sample holder 5 is provided, it is possible to more reliably prevent interference between the sample stage 6 and the sample holder 5.

Also, using a space made by removing the sample holder 5 (section shown by the dotted line in FIG. 2) to which the original sample 7 is fixed from the sample stage 6, the TEM sample 17 is fixed to a tip section 3b of the TEM sample holder 3a, which means that it is possible to cause the sample stage 6 to retreat from the FIB processing position. In this way, according to this embodiment, a movement space for the sample stage 6 for preventing interference that was required in the related art, that is, a space allowing sample stage 6 to retreat from the FIB processing position, is no longer required, which means that it is possible to make the device compact to the extent of that space.

Also, with this embodiment, a holding section 31 is provided on the TEM sample holder 3a in a detachable manner, which means that after TEM observation it is possible to re-use the TEM sample holder 3a by replacing the holding section 31 with a new one.

Figure 6:
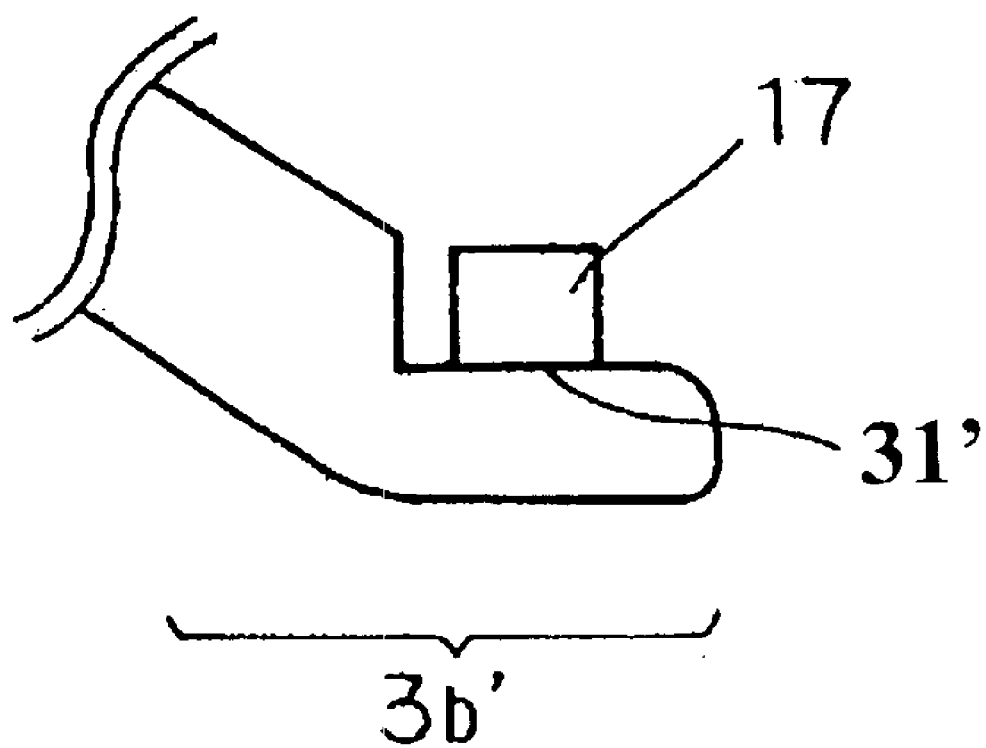
FIG. 6 is a schematic drawing showing one example of a TEM sample holder that can be used in the device shown in FIG. 1.

With this embodiment, the TEM sample 17 is fixed to the holding section 31 provided on the tip section 3b of the TEM sample holder 3a, but this is not limiting and appropriate modifications are possible to this structure. For example, as shown in FIG. 6, it is possible to use a TEM sample holder, provided with a fixing surface 31' that is parallel to the horizontal direction, on the tip section 3b', and to fix the TEM sample 17 directly to fixing surface 31'.

Description has been given above for manufacture of a TEM sample, but the present invention is not thus limited and a similar structure can also be applied to manufacture of an SEM sample. In case of manufacturing an SEM sample, it is possible to use an SEM sample holder shared between an SEM device and an FIB device, instead of the TEM sample holder. The SEM sample holder has basically the same structure as the TEM sample holder, except for being configured so as to fix an SEM sample that can be taken out from an original sample 7. An SEM sample is an observation slice of one side of the TEM sample 17.

(Embodiment 2)

With the above described first embodiment, a test piece (TEM sample or SEM sample) was taken out from the wafer, (being the original sample) using a manipulator, but it is also possible to take out the test piece with the observation sample holder itself, without using the manipulator. Here, description will be given for the state where it is possible to take out the test piece using the observation sample holder itself.

Figure 7:
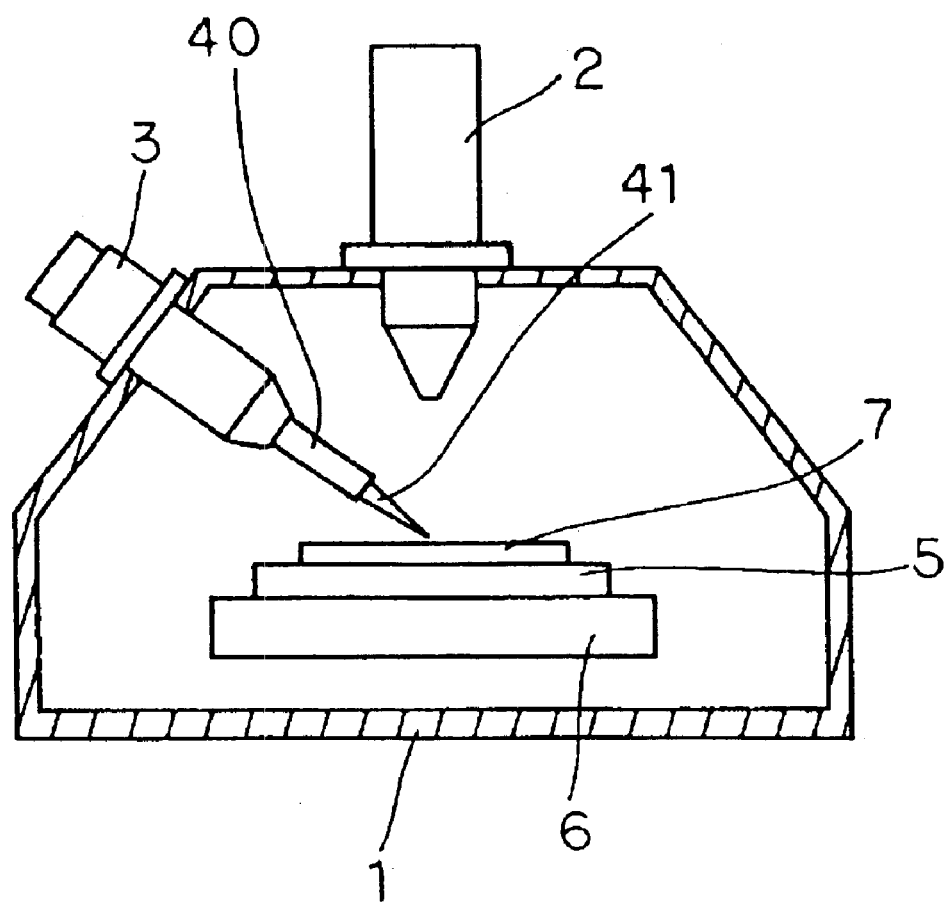
FIG. 7 is a schematic cross sectional drawing of the outline structure of an FIB device of a second embodiment of a sample manufacturing device of the present invention.

FIG. 7 is a schematic cross sectional drawing of the outline structure of an FIB device of a second embodiment of a sample manufacturing device of the present invention. With this FIB device, the manipulator is done away with from the structure shown in FIG. 1, and a TEM sample holder 40 having a needle 41 detachably provided on a tip section is attached to the side entry stage 3. In FIG. 7, the same reference numerals are attached to parts that are the same as in FIG. 1.

The needle 41 has a tapered tip, and an end opposite to the tip is fixed to the TEM sample holder 40. The TEM sample holder 40 can be shared between this FIB device and a TEM device. The side entry stage 3 is provided with a mechanism capable of moving the TEM sample holder 40 three dimensionally. A fine movement mechanism capable of bringing the tip of the needle 41 into contact with or close to a specified place of the original sample 7 is also contained in this movement mechanism.

Next, a description will be given of a manufacturing sequence for a TEM sample using this FIB device.

Figure 8A:
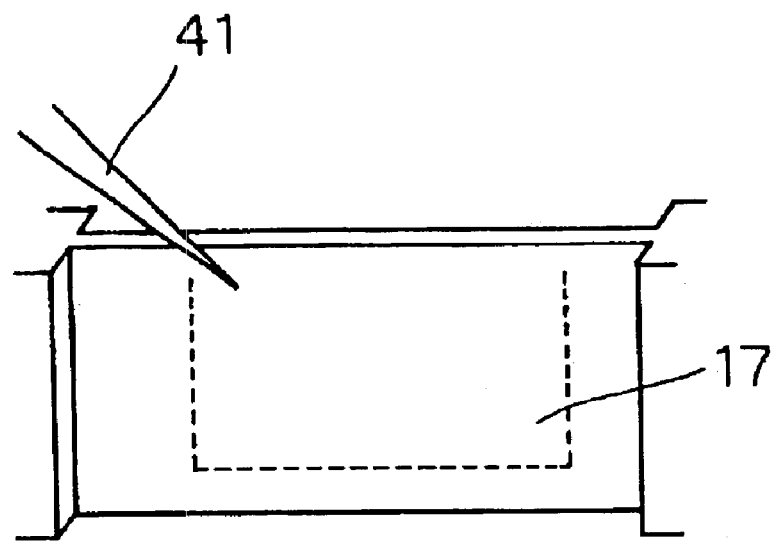
FIG. 8A and FIG. 8B are schematic drawings for describing a TEM sample fixing procedure carried out in the FIB device shown in FIG. 7.

First of all, similarly to the case of the first embodiment, after forming the TEM sample 17 shown in FIG. 4A, the TEM sample holder 40 is attached to the side entry stage 3. Then, in the side entry stage 3, by three-dimensionally controlling movement of the TEM sample holder 40, the tip of the needle 41 is brought into contact with a slice of the TEM sample 17, as shown in FIG. 8A. The contact position of the tip of the needle 41 constitutes a position such that final finishing processing, which will be described later, is not obstructed, for example, a corner of the slice of the TEM sample holder 40.

Figure 8B:
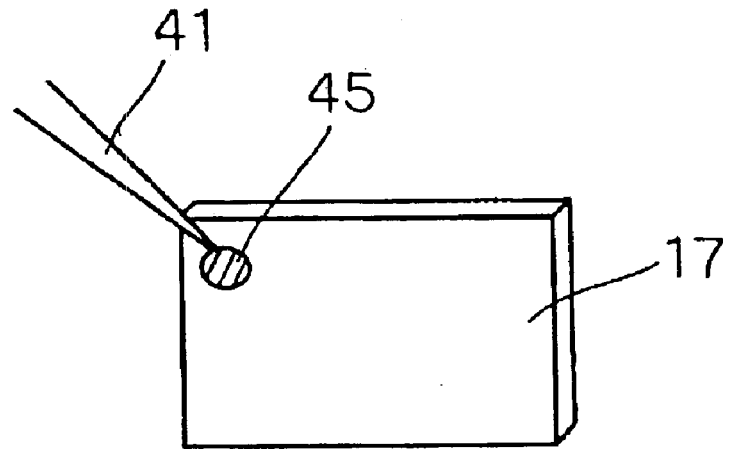

In the contact state described above, deposition gas is jetted to the contact section, and that section is also irradiated by an FIB from the FIB irradiation optical system 2, to selectively form a deposition film 45 as shown n FIG. 8B. The TEM sample 17 is fixed to the tip of the needle 41 by this deposition film 45, and it is possible to separate the TEM sample 17 from the wafer, being the sample. In fixing the TEM sample 17 to the tip of the needle 41, it is possible to use static electricity. Finally, both slice surfaces of the TEM sample 17 fixed to the needle 41 are subjected to final finishing processing using the FIB from the FIB irradiation optical system 2, to obtain an observation sample.

When carrying out TEM observation, the TEM sample holder 40 is removed from the side entry stage 3 and attached to the entry stage of the TEM device. Then, the observation slice of the TEM sample 17 is scanned by an electron beam inside the TEM device to obtain a TEM image.

After TEM observation, in the event that the TEM sample 17 is to be processed again, the TEM sample holder 40 is re-attached to the side entry stage 3.

With this embodiment also, similarly to the case of the first embodiment described above, the TEM sample holder 40, being the observation sample, is inserted diagonally from above the sample stage 6, which means that compared to the related art where the observation sample holder is inserted in the horizontal direction, it is difficult for the TEM sample holder 40 and the sample stage 6 to interfere with each other.

Also, since a movement space for the sample stage for preventing interference that was required in the related art is no longer required, it is possible to make the device compact to the extent of that space.

Further, with this embodiment, since the needle 41 is replaceable, it is possible to re-use the TEM sample holder 40 by replacing the needle 41 with a new one.

Also with this embodiment, since a manipulator is not required, it is possible to make the device compact and to lower cost by the extent of that manipulator, compared to the above described first embodiment.

Description has been given above for manufacture of a TEM sample, but similarly to the first embodiment, the present invention can also be applied to manufacture of an SEM sample.

(Embodiment 3)

Figure 9:
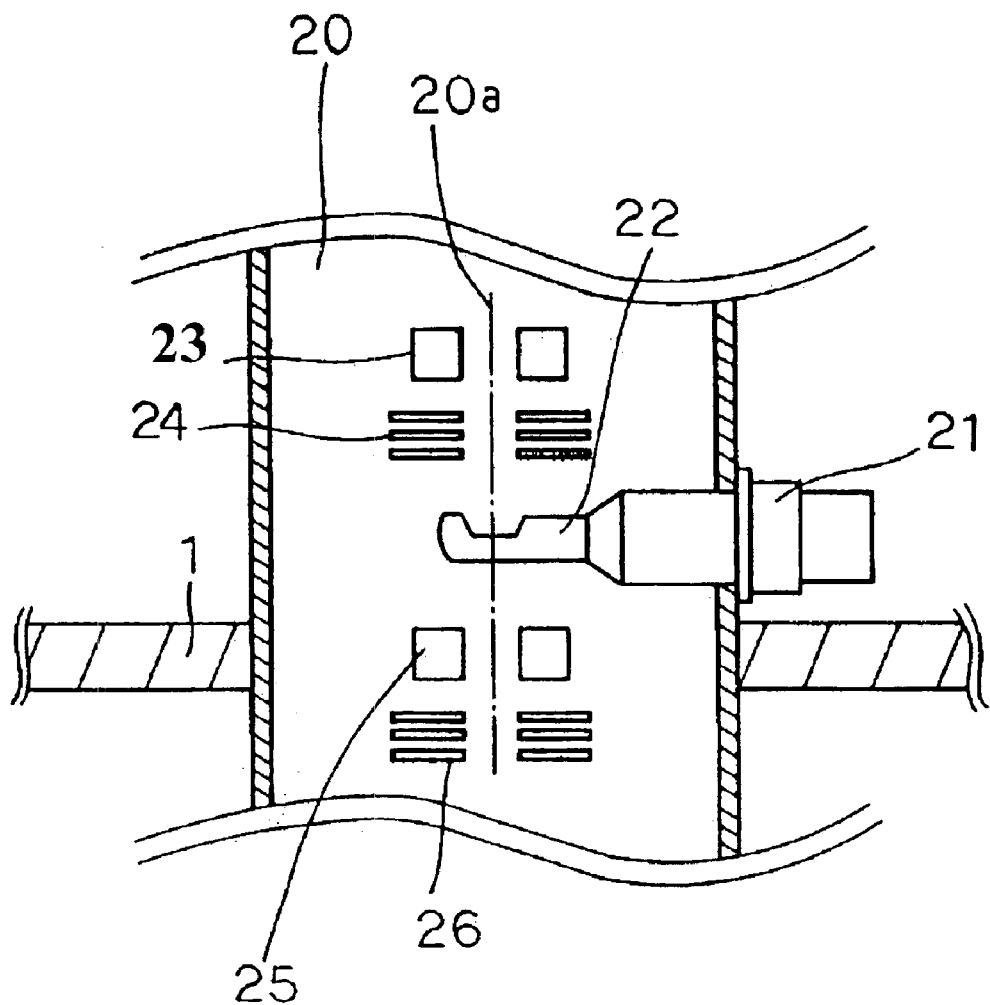
FIG. 9 is a schematic cross sectional drawing of the outline structure of an FIB device of a third embodiment of a sample manufacturing device of the present invention.

FIG. 9 is a schematic cross sectional drawing of the outline structure of an FIB device of a third embodiment of a sample manufacturing device of the present invention. With this FIB device, the FIB irradiation optical system 2 is done away with from the structure shown in FIG. 1, and apart from provision of an FIB irradiation optical system 20 having a lens barrel internal side entry stage 21, it is the same as the FIB device of the first embodiment described above.

The FIB irradiation optical system 20 is similar to the FIB irradiation optical system 2 shown in FIG. 1, and is attached to the sample chamber 1 so that it is possible to irradiate a specified location of an original sample 7 mounted on the sample stage 6 via the sample holder 5 with an ion beam, with the lens barrel internal side entry stage 21 being attached to a specified place of the lens barrel. The lens barrel internal side entry stage 21 can have an observation sample holder 22, constituted by the TEM sample holder or SEM sample holder described in the first embodiment above, attached, and it is possible to three dimensionally move this attached observation sample holder 22.

Also, the FIB irradiation optical system 20 has a structure where a first FIB irradiation section, made up of a deflection system 23 and an objective lens (electrostatic lens) 24, and a second FIB irradiation section, made up of a deflection system 25 and an objective lens (electrostatic lens) 26, are sequentially arranged in the advancing direction of an ion beam 20a emitted from an ion source (for example a Ga ion source), not shown. The first FIB irradiation section is for processing a test piece fixed to a tip section of the observation sample holder 22 inserted from the lens barrel internal side entry stage 21 with an ion beam 20a. The second FIB irradiation section is for processing a specified place of the original sample 7 on the sample stage 6 with the ion beam 20a, and processing the test piece fixed to the tip of the observation sample holder 22 inserted from the side entry stage 3 with the ion beam 20a.

With the FIB device of this embodiment, a test piece is manufactured by processing a specific site of the original sample 7 on the sample stage 6 using the first FIB irradiation section, and this manufactured test piece is fixed to a tip of the observation sample holder 22 inserted from the side entry stage 3. Also, the test piece fixed to the tip of the observation sample holder 22 is subjected to final finishing processing using the second FIB irradiation section. This test piece manufacture, fixing and finishing processing are similar to the case of the first embodiment described above.

When observing the test piece (for example, TEM observation or SEM observation), the observation sample holder 22 is removed from this FIB device, inserted into an entry stage of a separately prepared observation device (TEM device or SEM device), and the test piece that has been fixed to the tip of the observation sample holder 22 is observed with that observation device.

After observation, if the test piece is to be processed again, the observation sample holder 22 is removed from the observation device inserted into the lens barrel internal side entry stage 21 of this FIB device, and the test piece fixed to the tip of the observation sample holder 22 is subjected to processing again using the first FIB irradiation section.

The structure of the FIB device of the above described embodiment can also be applied to the FIB device of the above described second embodiment.

According to the FIB device of this embodiment, the freedom and precision of processing is improved compared to the above described first and second embodiments by providing the lens barrel internal side entry stage 21. The reason for this is that in the case of using the lens barrel internal side entry stage, since the TEM sample is arranged closer to the objective lens, the resolution becomes high compared to the side entry stage. Also, because stroke length of the observation sample holder of the lens barrel internal side entry stage is shorter than that of the side entry stage, there are also advantage with respect to vibration and rigidity. Still further, in the case of using an existing observation sample holder that does not have a holding section having a tilt mechanism, as shown in FIG. 3, processing of the TEM test piece with the lens barrel internal side entry stage results in higher processing precision than processing of the TEM test piece with the side entry stage.

As has been described above, according to the present invention, compare to the related art it is possible to more reliably prevent interference between a sample stage and an observation sample holder, to make a device more compact.

What is claimed is:

1. An apparatus for processing and observing a sample, the apparatus comprising:
   a sample stage for supporting a sample at a preselected location of the sample;
   a focused ion beam irradiation system for irradiating the sample with a focused ion beam along an optical axis to cut out a portion from the sample; and
   a side entry stage disposed over the sample stage and extending slantingly with respect to the optical axis of the focused ion beam irradiated by the focused ion beam irradiation system, the side entry stage having a microscope sample holder for picking up the cut-out sample portion directly from the preselected location of the sample and for supporting the sample portion, the microscope sample holder being configured to be removed from the side entry stage while supporting the sample portion and to be connected to an entry stage of a microscope device for observing the sample portion.

2. An apparatus according to claim 1; wherein the microscope sample holder has a needle removably connected to an end thereof for picking up the cut-out sample portion directly from the preselected location of the sample and for supporting the sample portion.

3. An apparatus according to claim 2; further comprising irradiating means for irradiating the sample portion with an ion beam which the sample portion is supported by the needle of the microscope sample holder.

4. An apparatus according to claim 2; wherein the irradiating means comprises the focused ion beam irradiation system.

5. An apparatus according to claim 1; further comprising irradiating means for irradiating the sample portion with an ion beam while the sample portion is supported by the needle of the microscope sample holder.

6. An apparatus according to claim 5; wherein the irradiating means comprises the focused ion beam irradiation system.

7. An apparatus according to claim 1; wherein the microscope sample holder comprises a transmission electron microscope sample holder.

8. An apparatus according to claim 1; wherein the microscope sample holder comprises a scanning electron microscope sample holder.

9. An apparatus according to claim 1; wherein the microscope sample holder has a needle removably connected to an end thereof; and further comprising a movement mechanism for controlling movement of the microscope sample holder to bring a tip of the needle into contact with the sample portion so that the tip of the needle picks up the sample portion directly from the preselected location of the sample and supports the sample portion.

10. An apparatus according to claim 9; further comprising means for supplying a deposition gas to a contact section between the tip of the needle and the sample portion, and irradiating means for irradiating with an ion beam the contact section supplied with the deposition gas to form a deposition film for integrally connecting the sample portion to the tip of the needle.

11. An apparatus according to claim 10; wherein the irradiating means comprises the focused ion beam irradiation system.

12. An apparatus according to claim 10; wherein the irradiating means includes means for irradiating the sample portion with an ion beam while the sample portion is integrally connected to the tip of the needle to thereby prepare the sample portion for observation by the microscopic device.

13. An apparatus according to claim 12; wherein the irradiating means comprises the focused ion beam irradiation system.

14. An apparatus according to claim 9; wherein the tip of the needle supports the sample portion by static electricity.

15. An apparatus for processing and observing a sample, the apparatus comprising:

a sample chamber;

a sample stage disposed in the sample chamber for supporting a sample;

a first focused ion beam irradiation system for irradiating the sample with a focused ion beam along an optical axis to cut out a portion from the sample;

a side entry stage disposed over the sample stage and extending slantingly with respect to the optical axis of the focused ion beam irradiated by the first focused ion beam irradiation system, the side entry stage having a removable sample holder for supporting the sample portion;

a second focused ion beam irradiation system for irradiating the sample portion with a focused ion beam while the sample portion is supported by the sample holder; and a single focused ion beam lens barrel having the first and second focused ion beam irradiation systems.

16. An apparatus according to claim 15; wherein the single focused ion beam lens barrel has an internal entry stage disposed between the first and second focused ion beam irradiation systems at a position outside of the sample chamber, the internal entry stage being configured to removably receive the sample holder.

17. An apparatus according to claim 16; wherein the second focused ion beam irradiation system irradiates the sample portion with the focused ion beam while the sample portion is supported by the sample holder and while the sample holder is removably received by the internal entry stage.

18. An apparatus according to claim 15; wherein the sample holder comprises a microscope sample holder configured to be removed from the side entry stage while supporting the sample portion and to be connected to an entry stage of a microscope device for observing the sample portion.

19. An apparatus according to claim 18; wherein the microscope sample holder comprises a transmission electron microscope sample holder.

20. An apparatus according to claim 18; wherein the microscope sample holder comprises a scanning electron microscope sample holder.

* * * * *